United States Patent
Braun et al.

(10) Patent No.: US 7,348,016 B2
(45) Date of Patent: Mar. 25, 2008

(54) SELF-REVERSIBLE REVERSE MICROLATEX, PROCESS FOR PREPARING THE SAME AND COSMETIC AND INDUSTRIAL USES THEREOF

(75) Inventors: Olivier Braun, Naves (FR); Paul Mallo, Chatou (FR); Guy Tabacchi, Paris (FR)

(73) Assignee: Societe d Exploitation de Produits pour les Industries Chimiques Seppic, Paris (FR)

( * ) Notice: Subject to any disclaimer, the term of this patent is extended or adjusted under 35 U.S.C. 154(b) by 686 days.

(21) Appl. No.: 10/459,082

(22) Filed: Jun. 10, 2003

(65) Prior Publication Data
US 2003/0235547 A1    Dec. 25, 2003

(30) Foreign Application Priority Data
Jun. 13, 2002   (FR) .................................. 02 07257

(51) Int. Cl.
- A61K 8/00   (2006.01)
- A61K 8/02   (2006.01)
- A61K 8/18   (2006.01)
- A61K 8/72   (2006.01)
- A61K 8/81   (2006.01)

(52) U.S. Cl. .................. 424/401; 424/70.1; 424/70.11; 424/70.16; 424/400; 514/844; 514/937; 514/939; 514/942; 514/944; 514/945

(58) Field of Classification Search ................ 424/401, 424/70.1, 70.11, 70.16, 400; 514/937, 844, 514/939, 942, 944, 945
See application file for complete search history.

(56) References Cited

U.S. PATENT DOCUMENTS

| | | | |
|---|---|---|---|
| 6,197,287 B1 * | 3/2001 | Mallo et al. ............ | 424/70.16 |
| 6,375,959 B1 | 4/2002 | Mallo et al. | |
| 7,033,600 B1 * | 4/2006 | Mallo et al. ................ | 424/401 |
| 2001/0051686 A1 | 12/2001 | Tabacchi et al. | |
| 2001/0053801 A1 | 12/2001 | Tabacchi et al. | |
| 2004/0191283 A1 * | 9/2004 | Roso et al. ................ | 424/401 |

FOREIGN PATENT DOCUMENTS

| | | |
|---|---|---|
| EP | 1010708 | 6/2000 |
| EP | 1152 022 A | 11/2001 |
| EP | 1152023 A | 11/2001 |
| FR | 2 774 688 A | 8/1999 |
| FR | 2785801 A | 5/2000 |
| GB | 0 503 853 * | 9/1992 |
| WO | WO 0032639 A | 6/2000 |

OTHER PUBLICATIONS

French Search Report to FR 02 07257.

* cited by examiner

*Primary Examiner*—Sreenivasan Padmanabhan
*Assistant Examiner*—Nathan W. Schlientz
(74) *Attorney, Agent, or Firm*—Young & Thompson

(57) ABSTRACT

A self-reversible reverse microlatex composition comprising an oil phase, an aqueous phase, at least one W/O surfactant, at least one O/W surfactant, and a branched or a crosslinked polyelectrolyte, wherein the W/O surfactant and the O/W surfactant mixture have a HLB from about 9.5 to about 10, and the polyelectrolyte is either a homopolymer or copolymer or a combination thereof based on at least one monomer containing a strong or weak acid function. Further, the composition may be used in the cosmetic, dermopharmaceutical, pharmaceutical, textile, paper, and/or paint industries, or as a thickener for printing pastes based on pigments or dyes.

36 Claims, No Drawings

SELF-REVERSIBLE REVERSE MICROLATEX, PROCESS FOR PREPARING THE SAME AND COSMETIC AND INDUSTRIAL USES THEREOF

The present patent application relates to thickening water-in-oil self-reversible reverse microlatices, to a process for preparing them and to their use as thickeners and/or emulsifiers for skincare and haircare products or for manufacturing cosmetic, dermopharmaceutical or pharmaceutical preparations, or textile treatment formulations.

Among the various existing thickeners used for thickening aqueous phases, there are polymers in powder form such as those described in the patent applications published under Nos. EP 0 341 660, EP 0 321 650 and EP 0 341 662 or the polymers described in FR 2 810 545.

Among the various existing thickeners for thickening aqueous phases, there are reverse emulsions of polymers such as those described in the patent applications published under Nos. EP 0 161 038, EP 0 503 853 or FR 2 790 759.

However, most of these thickeners have the drawback of still being very sensitive to the presence of salts.

In the course of research into the development of new polymers that are more resistant to the presence of salts, the Applicant became more particularly interested in reverse microemulsions of polymers and has found, unexpectedly, that some of them have improved stability to salts.

Accordingly, a subject of the invention is a composition comprising an oil phase, an aqueous phase, at least one surfactant of water-in-oil (W/O) type, at least one surfactant of oil-in-water (O/W) type and a branched or crosslinked polyelectrolyte, characterized in that (a) the said composition is a self-reversible reverse microlatex comprising from 15% to 40% by weight and preferably from 20% to 30% by weight of the said polyelectrolyte, (b) the said polyelectrolyte is either a homopolymer based on a monomer containing a strong acid function, which is partially or totally salified, or a copolymer based on at least one monomer containing a strong acid function, which is copolymerized either with at least one monomer containing a weak acid function or with at least one neutral monomer, or a copolymer based on at least one monomer containing a weak acid function, which is copolymerized with at least one neutral monomer, or a copolymer based on at least one monomer containing a strong acid function, which is copolymerized with a monomer containing at least one weak acid function and with at least one neutral monomer, and (c) the mixture of the said surfactant of water-in-oil (W/O) type and of the said surfactant of oil-in-water (O/W) type has a total HLB number of greater than or equal to 8.5 and less than or equal to 11 and preferably greater than or equal to 9.5 and less than or equal to 10.

The expression "surfactant of the water-in-oil type" denotes surfactants having an HLB value that is low enough to give water-in-oil emulsions, such as surfactant polymers of the polyethylene glycol poly(hydroxystearic acid) block copolymer type, sold under the name Hypermer™, such as sorbitan esters, for instance the sorbitan monooleate sold by the Applicant under the name Montane 80™, the sorbitan isostearate sold by the Applicant under the name Montane 70™, the sorbitan oleate ethoxylated with 5 mol of ethylene oxide (5 EO) sold by the Applicant under the name Montane™ 81, the diethoxylated (2 EO) oleocetyl alcohol sold by the Applicant under the name Simulsol™ OC 72 or the sorbitan sesquioleate sold by the Applicant under the name Montane™ 83.

The expression "surfactant of the oil-in-water type" denotes surfactants with an HLB value that is high enough to give oil-in-water emulsions such as ethoxylated sorbitan esters, for instance the sorbitan oleate ethoxylated with 20 mol of ethylene oxide (20 EO) sold by the Applicant under the name Montanox™ 80, the castor oil ethoxylated with 40 mol of ethylene oxide (40 EO) sold by the Applicant under the name Simulsol™ OL 50, the sorbitan laurate ethoxylated with 20 mol of ethylene oxide (20 EO), sold by the Applicant under the name Montanox™ 20, the sorbitan trioleate ethoxylated with 25 mol of ethylene oxide (25 EO) sold by the Applicant under the name Montanox™ 85, the lauryl alcohol ethoxylated with 7 mol of ethylene oxide (7 EO), sold by the Applicant under the name Simulsol™ P 7, the decaethoxylated (10 EO) oleocetyl alcohol sold by the Applicant under the name Simulsol™ OC 710 or the polyethoxylated sorbitan hexaoleoates sold under the names G-1086™ and G-1096™.

For the purposes of the present invention, the HLB number is calculated by means of the formula HLB=20 $(1-I_s/I_a)$, in which $I_s$ represents the saponification number of the surfactant or of the mixture of surfactants and $I_a$ represents the acid number of the starting fatty acid or of the mixture of starting fatty acids, as described by N. Schönfeld in the brochure entitled "Surface active ethylene oxide adducts" (page 228).

The term "branched polymer" denotes a non-linear polymer containing pendent chains so as to obtain, when this polymer is dissolved in water, a high degree of interlinking leading to very high viscosities at low rate gradient.

The term "crosslinked polymer" denotes a non-linear polymer in the form of a three-dimensional network, which is insoluble in water but swellable in water and thus leading to the production of a chemical gel.

The acid function of the monomer comprising it is especially the sulphonic acid function or the phosphonic acid function, which is partially or totally salified. The said monomer may be, for example, partially or totally salified styrene sulphonic acid or, preferably, partially or totally salified 2-methyl-2[(1-oxo-2-propenyl)amino]-1-propanesulphonic acid, especially in the form either of an alkali metal salt, for instance a sodium or potassium salt, or of an ammonium salt, or amino alcohol salt, for instance the monoethanolamine salt or an amino acid salt, for instance the lysine salt.

The weak acid function of the monomer comprising it is especially the carboxylic acid function, and the said monomer is preferably chosen from acrylic acid, methacrylic acid, itaconic acid, maleic acid or 3-methyl-3-[(1-oxo-2-propenyl)amino]butanoic acid, the said acids being partially or totally salified especially in the form either of an alkaline metal salt, for instance the sodium salt or the potassium salt, or of an ammonium salt, or an amino alcohol salt, for instance the monoethanolamine salt, or an amino acid salt, for instance the lysine salt.

The neutral monomer is especially chosen from acrylamide, 2-hydroxyethyl acrylate, 2,3-dihydroxypropyl acrylate, 2-hydroxyethyl methacrylate, 2-3-dihydroxypropyl methacrylate or an ethoxylated derivative with a molecular weight of between 400 and 1 000, of each of these esters.

According to a first particular aspect of the present invention, the polyelectrolyte included in the self-reversible reverse microlatex as defined above is a crosslinked 2-methyl-2-[(1-oxo-2-propenyl)amino]-1-propanesulphonic acid homopolymer partially or totally salified in the form of the sodium salt or the ammonium salt.

According to a second particular aspect of the present invention, the polyelectrolyte included in the self-reversible reverse microlatex as defined above, is a crosslinked copolymer of acrylic acid partially or totally salified in the form of the sodium salt or the ammonium salt (a) and of acrylamide (b), in an (a)/(b) molar ratio of between 10/90 and 90/10.

According to a third particular aspect of the present invention, the polyelectrolyte included in the self-reversible reverse microlatex as defined above is a crosslinked copolymer of 2-methyl-2-[(1-oxo-2-propenyl)amino]-1-propanesulphonic acid partially or totally salified in the form of the sodium salt, the ammonium salt, the monoethanolamine salt or the lysine salt (a) and of 2-hydroxyethyl acrylate (b), in an (a)/(b) molar ratio of between 30/70 and 90/10 and most particularly between 50/50 and 90/10.

According to a fourth particular aspect of the present invention, the polyelectrolyte included in the self-reversible reverse microlatex as defined above is a crosslinked copolymer of the sodium salt, the ammonium salt, the monoethanolamine salt or the lysine salt of 2-methyl-2-[(1-oxo-2-propenyl)amino]-1-propanesulphonic acid (a) and of acrylic acid partially or totally salified in the form of the sodium salt, the ammonium salt, the monoethanolamine salt or the lysine salt (c), in an (a)/(c) molar ratio of between 30/70 and 90/10 and most particularly between 30/70 and 45/55.

According to a fifth particular aspect of the present invention, the polyelectrolyte included in the reverse microlatex as defined above is a crosslinked copolymer of the sodium salt or the ammonium salt of 2-methyl-2-[(1-oxo-2-propenyl)amino]-1-propanesulphonic acid (a) and of acrylamide (d), in an (a)/(d) molar ratio of between 50/50 and 30/70.

According to a sixth particular aspect of the present invention, the polyelectrolyte included in the self-reversible reverse microlatex as defined above is a crosslinked copolymer of the sodium salt, the ammonium salt, the monoethanolamine salt or the lysine salt of 2-methyl-2-[(1-oxo-2-propenyl)amino]-1-propanesulphonic acid (a), of acrylic acid partially or totally salified in the form of the sodium salt, the ammonium salt, the monoethanolamine salt or the lysine salt (c) and either of acrylamide (d), or of 2-hydroxyethyl acrylate (e), in (a)/(c)+(d) or (a)/(c)+(e) molar proportions of between 10/90, 90/10 and (c)/(d) or (c)/(e) molar proportions of between 10/90 and 90/10.

A subject of the present invention is, more particularly, a composition as defined above, characterized in that the polyelectrolyte is crosslinked and/or branched with a diethylenic or polyethylenic compound in a molar proportion, expressed relative to the monomers used, of from 0.005% to 1%, more particularly from 0.01% to 0.5% and most particularly from 0.1% to 0.25%. The crosslinking agent and/or the branching agent is chosen from diallyloxyacetic acid or a salt thereof, for instance sodium diallyloxyacetate, ethylene glycol dimethacrylate, ethylene glycol diacrylate, diallylurea, trimethylolpropane triacrylate, methylenebis(acrylamide), triallylamine, and diallyl tartramide, or a mixture of these compounds.

The self-reversible reverse microlatex according to the invention generally contains between 8% and 20% by weight of surfactants.

The composition as defined above is characterized in that the oil phase represents from 25% to 50% and more particularly from 30% to 40% of its total weight.

This oil phase consists either of a commercial mineral oil containing saturated hydrocarbons, paraffins, isoparaffins or cycloparaffins, having at room temperature a density of between 0.7 and 0.9, and a boiling point of greater than 180° C., for instance Exxsol™ D100 S or Marcol™52 sold by Exxon Chemical, isohexadecane or isododecane, or of a plant oil, for instance squalane, or of a synthetic oil, for instance hydrogenated polyisobutene, or of a mixture of several of these oils.

Isohexadecane, which is identified in Chemical Abstracts by No. RN=93685-80-4, is a mixture of $C_{12}$, $C_{16}$ and $C_{20}$ isoparaffins containing at least 97% of $C_{16}$ isoparaffins, among which the main constituent is 2,2,4,4,6,8,8-heptamethylnonane (RN=4390-04-9). It is sold in France by the company Bayer. Marcol™52 is a commercial oil corresponding to the definition of liquid petroleum jellies in the French Codex. It is a white mineral oil in accordance with the regulations FDA 21 CFR 172.878 and CFR 178.3620 (a) and is recorded in the US Pharmacopoeia, US XXIII (1995) and in the European Pharmacopoeia (1993).

The self-reversible reverse microlatices according to the invention contain between 15% and 50% by weight of water.

The self-reversible reverse microlatices according to the invention may also contain various additives such as complexing agents, transfer agents or chain-limiting agents.

According to another aspect of the present invention, the invention relates to a process for preparing a reverse microemulsion of the polymer as defined above, characterized in that:

a) an oil phase and surfactants are added, with stirring to an aqueous solution containing the monomers and the optional additives, so as to form a reverse microemulsion, and then b) the polymerization reaction is initiated and the said reaction is then left to proceed to form the reverse microlatex.

According to one preferred embodiment of the process as defined above, the polymerization reaction is initiated by a redox couple, such as the cumin hydroperoxide/sodium metabisulphite couple, at a temperature of less than or equal to 20° C., and then formed either virtually adiabatically up to a temperature of greater than or equal to 40° C., more particularly greater than or equal to 50° C., or by controlling the change in temperature.

A subject of the invention is also a cosmetic, dermopharmaceutical or pharmaceutical composition, characterized in that it comprises at least one reverse microlatex as defined above as thickening and/or emulsifying compound.

The cosmetic, dermocosmetic, dermopharmaceutical or pharmaceutical composition defined above generally comprises from 0.1% to 10% and more particularly between 0.5% and 5% by weight of the said reverse microlatex. It is especially in the form of a milk, a lotion, a gel, a cream, a soap, a bubble-bath, a balm, a shampoo or a conditioner.

In general, the said reverse microlatex may advantageously replace the products sold under the name Sepigel™ 305 or Sepigel™ 501 by the Applicant, in cosmetic, dermopharmaceutical or pharmaceutical compositions, since it also shows good compatibility with the other excipients used for preparing formulations such as milks, lotions, creams, soaps, bubble-baths, balms, shampoos or conditioners. It may also be used in combination with the said Sepigel products. It is especially compatible with the concentrates described and claimed in the international publications WO 92/06778, WO 95/04592 and WO 95/13863 or FR 2 734 496 or with the surfactants described in WO 93/08204. It is particularly compatible with Montanov™ 68, Montanov™ 82, Montanov™ 202, Montanov™ WO18, Montanov™ S or Sepiperl™ N. It may also be used in emulsions of the type described and claimed in EP 0 629 396 and in cosmetically or physiologically acceptable aqueous dispersions with an organopolysiloxane compound chosen, for example, from those described in WO 93/05762 or in WO 93/21316. It may also be used to form cosmetically or physiologically acceptable aqueous gels at acidic pH, such as those described in WO 93/07856; it may also be used in combination with nonionic celluloses, for example to form styling gels, such as those described in EP 0 684 024 or in combination with fatty acid esters of sugars, to form compositions for treating the hair or the skin such as those described in EP 0 603 019, or in shampoos or conditioners as described and claimed in WO 92/21316 or, finally, in combination with an anionic homopolymer, such as the Carbopol™ products to form hair treatment products, for instance those described in DE 195 23 596. It is also compatible with numerous active principles, for instance self-tanning agents such as dihydroxyacetone (DHA) or antiacne agents; it may thus be introduced into self-tanning compositions such as those claimed in EP 0 715 845, EP 0 604 249 or EP 0 576 188 or in WO 93/07902. It is also compatible with N-acyl derivatives of amino acids, which allows its use in calmant compositions especially for sensitive skin, such as those described or claimed in WO 92/21318, WO 94/27561 or WO 98/09611. It is also compatible with glycolic acids, with lactic acid, with salicylic acid, retinoids, phenoxyethanol, sugars, glyceraldehyde, xanthans, fruit acids, and the various polyols used in the manufacture of cosmetic formulations.

A subject of the invention is thus also the use of a reverse microlatex as defined above as an emulsifier and/or thickener, in the preparation of a cosmetic, dermocosmetic, dermopharmaceutical or pharmaceutical composition.

According to a final aspect of the present invention, a subject of this invention is the use of the composition as defined above as a thickener and/or emulsifier in preparations intended for industries of all kinds, whether it is, for example, the textile industry, the paper industry or the paint manufacturing industry.

According to a particular aspect of this final aspect of the present invention, its subject is the use of a self-reversible reverse microlatex as a thickener for printing pastes or for paint manufacture, and more particularly as a thickener for printing pastes based on pigments or dyes. Such pastes are especially used in the textile industry. The examples that follow are aimed at illustrating the present invention without, however, limiting it.

EXAMPLE 1

Preparation and Properties of the Reverse Microlatex (A) According to the Invention Preparation The following are loaded into a beaker, with stirring:
0.26 g of methylenebis(acrylamide),
0.45 g of a commercial solution containing 40% by weight of sodium diethylenetriaminepentaacetate,
121.9 g of a commercial 50% acrylamide solution, and
358.1 g of a commercial solution containing 55% by weight of the sodium salt of 2-methyl-2-[(1-oxo-2-propenyl)amino]-1-propanesulphonic acid (55% Na ATBS).

The following are successively added to this aqueous phase, with simple stirring:
393 g of isohexadecane,
25.2 g of Montane™ 80 VG,
116.2 g of Montanox™ 80,
0.41 g of AIBN (azobis(isobutyronitrile)), and a clear reverse microemulsion is obtained.

The microemulsion obtained is transferred into a polymerization reactor and nitrogen is bubbled through for 1 hour. 2.4 g of a solution containing 1% by weight of cumin hydroperoxide in isohexadecane are then added, followed by addition of an aqueous sodium metabisulphite solution (0.2 g in 100 ml of water) at a rate of 0.5 ml/minute. The introduction is performed over about 10 minutes. At the end of polymerization, a transparent, stable self-reversible reverse microlatex is obtained.

Evaluation of the Properties

Viscosity of the self-reversible reverse microlatex containing 1% polymer in water (Brookfield RVT, spindle No. 5; speed: 5 rpm): $\eta=98\ 000$ mPa·s;

Viscosity of the self-reversible reverse microlatex containing 1% polymer in water+0.1% NaCl (Brookfield RVT, spindle No. 5; speed: 5 rpm); $\eta=29\ 400$ mPa·s;

Ratio R: viscosity in the saline solution/viscosity in water=0.3.

For comparative purposes, the viscosities at 1% in water and at 1% in water+0.1% NaCl, of a self-reversible reverse latex of a crosslinked copolymer prepared with the same monomers in the same molar proportions (50/50 acrylamide/ ATBS) and the same crosslinking agent (methylenebis(acrylamide)), in the same oil (ioshexadecane), were measured. The results are given in the table below.

|  | Self-reversible reverse microlatex (invention) | Self-reversible reverse latex (prior art) |
|---|---|---|
| Viscosity at 1% in water (RVT spindle 6, speed 5) | 98 000 mPa s | 74 800 mPa s |
| Viscosity at 1% in water + 0.1% NaCl (RVT spindle 5, speed 5) | 29 400 mPa s | 4 400 mPa s |
| Ratio R | 0.3 | 0.06 |

These results show that the reverse microlatex of the invention is much more stable to salt than the reverse latex of the same copolymer in the same oil at similar concentrations.

EXAMPLE 2

Preparation and Properties of the Reverse Microlatex (B) According to the Invention Preparation The following are loaded into a beaker, with stirring:
0.40 g of methylenebis(acrylamide),
0.45 g of a commercial solution containing 40% by weight of sodium diethylenetriaminepentaacetate,
0.55 g of 2-methyl-2-[(1-oxo-2-propenyl)amino]-1-propanesulphonic acid, and
540 g of a commercial solution containing 55% by weight of the sodium salt of 2-methyl-2-[(1-oxo-2-propenyl) amino]-1-propanesulphonic acid (55% Na ATBS).

The following are successively added to this aqueous phase, with simple stirring:
360 g of isohexadecane,
17.9 g of Montane™ 80 VG,
82.9 g of Montanox™ 85,
0.41 g of AIBN
and a clear reverse microemulsion is obtained.

The microemulsion obtained is transferred into a polymerization reactor and nitrogen is bubbled through for 1 hour. 2.4 g of a solution containing 1% by weight of cumin hydroperoxide in isohexadecane are then added, followed by addition of an aqueous sodium metabisulphite solution (0.2 g in 100 ml of water) at a rate of 0.5 ml/minute. The introduction is performed over about 10 minutes. At the end of polymerization, a transparent, stable self-reversible reverse microlatex is obtained.

Evaluation of the Properties

Viscosity of the self-reversible reverse microlatex containing 1% polymer in water (Brookfield RVT, spindle No. 5; speed: 5 rpm): $\eta = 52\,000$ mPa·s;

Viscosity of the self-reversible reverse microlatex containing 1% polymer in water+0.1% NaCl (Brookfield RVT, spindle No. 5; speed: 5 rpm); $\eta = 15\,000$ mPa·s;

Ratio: viscosity in the saline solution/viscosity in water=0.3.

For comparative purposes, the viscosities at 1% in water and at 1% in water+0.1% NaCl, of a self-reversible reverse latex of a crosslinked homopolymer prepared with the same monomer and the same crosslinking agent (methylenebis(acrylamide), in the same oil (ioshexadecane), were measured. The results are given in the table below.

|  | Self-reversible reverse microlatex (invention) | Self-reversible reverse latex (prior art) |
|---|---|---|
| Viscosity at 1% in water (RVT spindle 6, speed 5) | 52 000 mPa s | 100 000 mPa s |
| Viscosity at 1% in water + 0.1% NaCl (RVT spindle 5, speed 5) | 15 000 mPa s | 6 200 mPa s |
| Ratio R | 0.3 | 0.06 |

These results show that the reverse microlatex of the invention is much more stable to salt than the reverse latex of the same homopolymer in the same oil at similar concentrations.

EXAMPLE 3

Preparation and Properties of the Reverse Microlatex (C) According to the Invention Preparation The following are loaded into a beaker, with stirring:

0.26 g of methylenebis(acrylamide), 0.45 g of a commercial solution containing 40% by weight of sodium diethylenetriaminepentaacetate, 120.2 g of a commercial 50% acrylamide solution, and 352.8 g of a commercial solution containing 55% by weight of the sodium salt of 2-methyl-2-[(1-oxo-2-propenyl)amino]-1-propanesulphonic acid (55% Na ATBS), and 0.4 g of 2-methyl-2-[(1-oxo-2-propenyl)amino]-1-propanesulphonic acid.

The following are successively added to this aqueous phase, with simple stirring:

387.1 g of hydrogenated polyisobutene (PIB), 39.7 g of Montane™ 80 VG, 100.3 g of Montanox™ 85, 0.4 g of AIBN, and a clear reverse microemulsion is obtained.

The microemulsion obtained is transferred into a polymerization reactor and nitrogen is bubbled through for 1 hour. 2.4 g of a solution containing 1% by weight of cumin hydroperoxide in PIB are then added, followed by addition of an aqueous sodium metabisulphite solution (0.2 g in 100 ml of water) at a rate of 0.5 ml/minute. The introduction is performed over about 10 minutes. At the end of polymerization, a transparent, stable self-reversible reverse microlatex is obtained.

Evaluation of the Properties

Viscosity of the self-reversible reverse microlatex containing 1% polymer in water (Brookfield RVT, spindle No. 6; speed: 5 rpm): $\eta = 72\,000$ mPa·s;

Viscosity of the self-reversible reverse microlatex containing 1% polymer in water+0.1% NaCl (Brookfield RVT, spindle No. 6; speed: 5 rpm); $\eta = 21\,000$ mPa·as;

Ratio: viscosity in the saline solution/viscosity in water=0.3.

C) Examples of Formulations Prepared with the Compositions According to the Invention

EXAMPLE 4

Care Cream

| | |
|---|---|
| Cyclomethicone: | 10% |
| Reverse microlatex A: | 0.8% |
| Montanov ™ 68: | 2% |
| Stearyl alcohol: | 1% |
| Stearyl alcohol: | 0.5% |
| Preserving agent: | 0.65% |
| Lysine: | 0.025% |
| EDTA (disodium salt): | 0.05% |
| Xanthan gum: | 0.2% |
| Glycerol: | 3% |
| Water: | q.s. 100% |

EXAMPLE 5

Aftershave Balm

| | FORMULA | |
|---|---|---|
| A | Reverse microlatex A: | 1.5% |
|   | Water: | q.s. 100% |
| B | Micropearl ™ M 100: | 5.0% |
|   | Sepicide ™ CI: | 0.50% |
|   | Fragrance: | 0.20% |
|   | 95° ethanol: | 10.0% |

Procedure

Add B to A.

EXAMPLE 6

Satin Body Emulsion

| | FORMULA | |
|---|---|---|
| A | Simusol ™ 165: | 5.0% |
| | Lanol ™ 1688: | 8.50% |
| | Karite butter: | 2% |
| | Liquid paraffin: | 6.5% |
| | Lanol ™ 14M: | 3% |
| | Lanol ™ S: | 0.6% |
| B | Water: | 66.2% |
| C | Micropearl ™ M 100: | 5% |
| D | Reverse microlatex C: | 3% |
| E | Sepicide ™ CI: | 0.3% |
| | Sepicide ™ HB: | 0.5% |
| | Monteine ™ CA: | 1% |
| | Fragrance: | 0.20% |
| | Vitamin E acetate: | 0.20% |
| | Sodium pyrrolidinonecarboxylate: | 1% |

Procedure

Add C to B, emulsify B in A at 70° C. and then add D at 60° C., followed by E at 30° C.

EXAMPLE 7

O/W Cream

| | FORMULA | |
|---|---|---|
| A | Simulsol ™ 165: | 5.0% |
| | Lanol ™ 1688: | 20.0% |
| | Lanol ™ P: | 1.0% |
| B | Water: | q.s. 100% |
| C | Reverse microlatex C: | 2.50% |
| D | Sepicide ™ CI: | 0.20% |
| | Sepicide ™ HB: | 0.30% |

Procedure

Introduce B into A at about 75° C.; add C at about 60° C., followed by D at 45° C.

EXAMPLE 8

Non-Greasy Antisun Gel

| | FORMULA | |
|---|---|---|
| A | Reverse microlatex B: | 3.00% |
| | Water: | 30% |
| B | Sepicide ™ CI: | 0.20% |
| | Sepicide ™ HB: | 0.30% |
| | Fragrance: | 0.10% |
| C | Dye: | q.s. |
| | Water: | 30% |
| D | Micropearl ™ M 100: | 3.00% |
| | Water: | q.s. 100% |
| E | Silicone oil: | 2.0% |
| | Parsol ™ MCX: | 5.00% |

Procedure

Introduce B into A; add C, followed by D and then E.

EXAMPLE 9

Antisun Milk

| | FORMULA | |
|---|---|---|
| A | Montanov ™ S: | 3.0% |
| | Sesame oil: | 5.0% |
| | Parsol ™ MCX: | 5.0% |
| | λ-Carrageenan | 0.10% |
| B | Water: | q.s. 100% |
| C | Reverse microlatex A: | 0.80% |
| D | Fragrance: | q.s. |
| | Preserving agent: | q.s. |

Procedure

Emulsify B in A at 75° C., then add C at about 60° C., followed by D at about 30° C., and adjust the pH if necessary.

EXAMPLE 10

Massage Gel

| | FORMULA | |
|---|---|---|
| A | Reverse microlatex B: | 3.5% |
| | Water: | 20.0% |
| B | Dye: | 2 drops/100 g |
| | Water: | q.s. |
| C | Alcohol: | 10% |
| | Menthol: | 0.10% |
| D | Silicone oil: | 5.0% |

Procedure

Add B to A, then add C to the mixture, followed by D.

EXAMPLE 11

Moisturizing and Matting Foundation

| | FORMULA | |
|---|---|---|
| A | Water: | 20.0% |
| | Butylene glycol: | 4.0% |
| | PEG-400: | 4.0% |
| | Pecosil ™ PS100: | 1.0% |
| | NaOH: | q.s. pH = 9 |
| | Titanium dioxide: | 7.0% |
| | Talc: | 2.0% |
| | Yellow iron oxide: | 0.8% |
| | Red iron oxide: | 0.3% |
| | Black iron oxide: | 0.05% |
| B | Lanol ™ 99: | 8% |
| | Caprylic/capric triglyceride | 8% |
| | Montanov ™ 202: | 5.00% |
| C | Water: | q.s. 100% |
| | Micropearl ™ M305: | 2.0% |
| | Tetrasodium EDTA: | 0.05% |

-continued

| | FORMULA | |
|---|---|---|
| D | Cyclomethicone: | 4.0% |
| | Xanthan gum: | 0.2% |
| | Reverse microlatex A: | 0.8% |
| E | Sepicide ™ HB: | 0.5% |
| | Sepicide CI: | 0.3% |
| | Fragrance: | 0.2% |

Procedure

Prepare the mixtures B+D and A+C at 80° C., then mix together and emulsify.

EXAMPLE 12

Radiant-Effect Gel

| | FORMULA | |
|---|---|---|
| A | Reverse microlatex C: | 4% |
| | Water: | 30% |
| B | Elastine HPM: | 5.0% |
| C | Micropearl ™ M 100: | 3% |
| | Water: | 5% |
| D | Sepicide ™ CI: | 0.2% |
| | Sepicide ™ HB: | 0.3% |
| | Fragrance: | 0.06% |
| | 50% sodium pyrrolidinonecarboxylate: | 1% |
| | Water: | q.s. 100% |

Procedure

Prepare A; add B, followed by C and then D.

EXAMPLE 13

Body Milk

| | FORMULA | |
|---|---|---|
| A | Montanov ™ S: | 3.5% |
| | Lanol ™ 37T: | 8.0% |
| | Solagum ™ L: | 0.05% |
| | Water: | q.s. 100% |
| | Benzophenone: | 2.0% |
| | Dimethicone 350 cPs: | 0.05% |
| | Reverse microlatex B: | 0.08% |
| | Preserving agent: | 0.2% |
| | Fragrance: | 0.4% |

EXAMPLE 14

Make-Up-Removing Emulsion Containing Sweet Almond Oil

| FORMULA | |
|---|---|
| Montanov ™ 68: | 5% |
| Sweet almond oil: | 5% |
| Water: | q.s. 100% |

-continued

| FORMULA | |
|---|---|
| Reverse microlatex A: | 0.3% |
| Glycerol: | 5% |
| Preserving agent: | 0.2% |
| Fragrance: | 0.3% |

EXAMPLE 15

Moisturizing Cream for Greasy Skin

| FORMULA | |
|---|---|
| Montanov ™ 68: | 5% |
| Cetylstearyl octanoate: | 8% |
| Octyl palmitate: | 2% |
| Water: | q.s. 100% |
| Reverse microlatex C: | 0.6% |
| Micropearl ™ M100: | 3.0% |
| Mucopolysaccharides: | 5% |
| Sepicide ™ HB: | 0.8% |
| Fragrance: | 0.3% |

EXAMPLE 16

Alcohol-Free, Soothing After-Shave Balm

| | FORMULA | |
|---|---|---|
| A | Lipacide ™ PVB: | 1.0% |
| | Lanol ™ 99: | 2.0% |
| | Sweet almond oil: | 0.5% |
| B | Reverse microlatex A: | 3.5% |
| C | Water: | q.s. 100% |
| D | Fragrance: | 0.4% |
| | Sepicide ™ HB: | 0.4% |
| | Sepicide ™ CI: | 0.2% |

EXAMPLE 17

Cream Containing AHAs for Sensitive Skin

| FORMULA | |
|---|---|
| Mixture of laurylamino acids: | 0.1% to 5% |
| Magnesium potassium aspartate: | 0.002% to 0.5% |
| Lanol ™ 99: | 2% |
| Montanov ™ 68: | 5.0% |
| Water: | q.s. 100% |
| Reverse microlatex B: | 1.50% |
| Gluconic acid: | 1.50% |
| Triethylamine: | 0.9% |
| Sepicide ™ HB: | 0.3% |
| Sepicide ™ CI: | 0.2% |
| Fragrance: | 0.4% |

EXAMPLE 18

Aftersun Soothing Care Product

| FORMULA | |
|---|---|
| Mixture of lauryl amino acids: | 0.1% to 5% |
| Magnesium potassium aspartate: | 0.002% to 0.5% |
| Lanol ™ 99: | 10.0% |
| Water: | q.s. 100% |
| Reverse microlatex A: | 2.50% |
| Sepicide ™ HB: | 0.3% |
| Sepicide ™ CI: | 0.2% |
| Fragrance: | 0.4% |
| Dye: | 0.03% |

EXAMPLE 19

Make-Up-Removing Milk

| FORMULA | |
|---|---|
| Sepiperl ™ N: | 3% |
| Primol ™ 352: | 8.0% |
| Sweet almond oil: | 2% |
| Water: | q.s. 100% |
| Reverse microlatex B: | 0.8% |
| Preserving agent: | 0.2% |

EXAMPLE 20

Alkaline-pH Fluid Emulsion

| FORMULA | |
|---|---|
| Marcol ™ 82: | 5.0% |
| NaOH: | 10.0% |
| Water: | q.s. 100% |
| Reverse microlatex A: | 1.5% |

EXAMPLE 21

Fluid Foundation

| FORMULA | |
|---|---|
| Simusol ™ 165: | 5.0% |
| Lanol ™ 84D: | 8.0% |
| Lanol ™ 99: | 5.0% |
| Water: | q.s. 100% |
| Inorganic fillers and pigments: | 10.0% |
| Reverse microlatex A: | 1.2% |
| Preserving agent: | 0.2% |
| Fragrance: | 0.4% |

EXAMPLE 22

Antisun Milk

| FORMULA | |
|---|---|
| Sepiperl ™ N: | 3.5% |
| Lanol ™ 37T: | 10.0% |
| Parsol ™ MCX: | 5.0% |
| Eusolex ™ 4360: | 2.0% |
| Water: | q.s. 100% |
| Reverse microlatex A: | 1.8% |
| Preserving agent: | 0.2% |
| Fragrance: | 0.4% |

EXAMPLE 23

Gel for Around the Eyes

| FORMULA | |
|---|---|
| Reverse microlatex A: | 2.0% |
| Fragrance: | 0.06% |
| Sodium pyrrolidinonecarboxylate: | 0.2% |
| Dow Corning ™ 245 Fluid | 2.0% |
| Water: | q.s. 100% |

EXAMPLE 24

Leave-in Care Composition

| FORMULA | |
|---|---|
| Reverse microlatex C: | 1.5% |
| Fragrance: | q.s. |
| Preserving agent: | q.s. |
| Dow Corning ™ X2 8360: | 5.0% |
| Dow Corning ™ Q2 1401: | 15.0% |
| Water: | q.s. 100% |

EXAMPLE 25

Slimming Gel

| | |
|---|---|
| Reverse microlatex C: | 5% |
| Ethanol: | 30% |
| Menthol: | 0.1% |
| Caffeine: | 2.5% |
| Extract of butcher's-broom: | 2% |
| Extract of ivy: | 2% |
| Sepicide ™ HP: | 1% |
| Water: | q.s. 100% |

EXAMPLE 26

Ultra-Natural Tinted Cream Gel

| | FORMULA | |
|---|---|---|
| A | Water: | 10.0% |
| | Butylene glycol: | 4.0% |
| | PEG-400: | 4.0% |
| | Pecosil ™ PS100: | 1.5% |
| | NaOH: | q.s. pH = 7 |
| | Titanium dioxide: | 2.0% |
| | Yellow iron oxide: | 0.8% |
| | Red iron oxide: | 0.3% |
| | Black iron oxide: | 0.05% |
| B | Lanol ™ 99: | 4.0% |
| | Caprylic/capric triglyceride: | 4.0% |
| | Sepifeel ™ One: | 1.0% |
| | Reverse microlatex B: | 3.0% |
| C | Water: | q.s. 100% |
| | Micropearl ™ M305: | 2.0% |
| | Tetrasodium EDTA: | 0.05% |
| | Cyclomethicone: | 4.0% |
| D | Sepicide ™ HB: | 0.5% |
| | Sepicide CI: | 0.3% |
| | Fragrance: | 0.2% |

Procedure

Prepare the mixture B+C then add A, followed by D.

EXAMPLE 27

Care Product for Greasy Skin

| | FORMULA | |
|---|---|---|
| A | Micropearl ™ M310: | 1.0% |
| | Reverse microlatex A: | 5.0% |
| | Octyl isononanoate: | 4.0% |
| B | Water: | q.s. 100% |
| C | Sepicontrol ™ A5: | 4.0% |
| | Fragrance: | 0.1% |
| | Sepicide ™ HB: | 0.3% |
| | Sepicide ™ CI: | 0.2% |
| D | Capigel ™ 98: | 0.5% |
| | Water: | 10% |

EXAMPLE 28

Cream Containing AHAs

| | FORMULA | |
|---|---|---|
| A | Montanov ™ 68: | 5.0% |
| | Lipacide ™ PVB: | 1.05% |
| | Lanol ™ 99: | 10.0% |
| B | Water: | q.s. 100% |
| | Gluconic acid: | 1.5% |
| | TEA (triethanolamine): | 0.9% |
| C | Reverse microlatex B: | 1.5% |
| D | Fragrance: | 0.4% |
| | Sepicide ™ HB: | 0.2% |
| | Sepicide ™ CI: | 0.4% |

EXAMPLE 29

Non-Greasy Self-Tanning Product for the Face and the Body

| | FORMULA | |
|---|---|---|
| A | Lanol ™ 2681: | 3.0% |
| | Reverse microlatex A: | 2.5% |
| B | Water: | q.s. 100% |
| | Dihydroxyacetone: | 3.0% |
| C | Fragrance: | 0.2% |
| | Sepicide ™ HB: | 0.8% |
| | NaOH (sodium hydroxide): | q.s. pH = 5 |

EXAMPLE 30

Antisun Milk Containing Monoï de Tahiti

| | FORMULA | |
|---|---|---|
| A | Monoï de Tahiti: | 10% |
| | Lipacide ™ PVB: | 0.5% |
| | Reverse microlatex B: | 2.2% |
| B | Water: | q.s. 100% |
| C | Fragrance: | 0.1% |
| | Sepicide ™ HB: | 0.3% |
| | Sepicide ™ CI: | 0.1% |
| | Parsol ™ MCX: | 4.0% |

EXAMPLE 31

Antisun Care Product for the Face

| | FORMULA | |
|---|---|---|
| A | Cyclomethicone and dimethiconol: | 4.0% |
| | Reverse microlatex B: | 3.5% |
| B | Water: | q.s. 100% |
| C | Fragrance: | 0.1% |
| | Sepicide ™ HB: | 0.3% |
| | Sepicide ™ CI: | 0.21% |
| | Parsol ™ MCX: | 5.0% |
| | Titanium mica: | 2.0% |
| | Lactic acid: | q.s. pH = 6.5 |

EXAMPLE 32

Self-Tanning Emulsion

| | FORMULA | |
|---|---|---|
| A | Lanol ™ 99: | 15% |
| | Montanov ™ 68: | 5.0% |
| | Parsol ™ MCX: | 3.0% |
| B | Water: | q.s. 100% |
| | Dihydroxyacetone: | 5.0% |
| | Monosodium phosphate: | 0.2% |
| C | Reverse microlatex A: | 0.5% |
| D | Fragrance: | 0.3% |
| | Sepicide ™ HB: | 0.8% |
| | NaOH: | q.s. pH = 5 |

The characteristics of the products used in the above examples are as follows:

Montanov™ 68 (cetearyl glucoside, cetearyl alcohol) is a self-emulsifying composition as described in WO 92/06778, sold by the company SEPPIC.

Montanov™ 202 (arachidyl glucoside, arachidyl alcohol+ behenyl alcohol) is a self-emulsifying composition such as those described in WO 98/17610, sold by the company SEPPIC.

Micropearl™ M 305 is a silky water-dispersible powder based on crosslinked methyl methacrylate copolymer.

Micropearl™ M100 is an ultra-fine powder with a very soft feel sensation and a matt effect, sold by the company Matsumo.

Sepicide™ CI, imidazolinurea, is a preserving agent sold by the company SEPPIC.

Pemulen™ TR is an acrylic polymer sold by Goodrich.

Simulsol™ 165 is self-emulsifying glyceryl stearate, sold by the company SEPPIC.

Lanol™ 1688 is a non-greasy emollient ester sold by the company SEPPIC.

Lanol™ 14M and Lanol™ S are consistency factors sold by the company SEPPIC.

Sepicide™ HB, which is a mixture of phenoxyethanol, methylparaben, ethylparaben, propylparaben and butylparaben, is a preserving agent sold by the company SEPPIC.

Monteine™ CA is a moisturizer sold by the company SEPPIC.

Schercemol™ OP is a non-greasy emollient ester.

Lanol™ P is a stabilizing additive sold by the company SEPPIC.

Sepiperl™ N is a pearlescent agent, sold by the company SEPPIC, based on a mixture of alkylpolyglucosides such as those described in WO 95/13863.

Montanov™ S is a pearlescent agent, sold by the company SEPPIC, based on a mixture of alkylpolyglucosides such as those described in WO 95/13863.

Pecosil™ PS100 is dimethicone copolyol phosphate sold by the company Phoenix.

Lanol™ 99 is isononyl isononanoate, sold by the company SEPPIC.

Lanol™ 37T is glyceryl triheptanoate, sold by the company SEPPIC.

Sepifeel™ ONE is a mixture of palmitoylproline, magnesium palmitoyl glutamate and magnesium palmitoyl sarcosinate, such as those described in FR 2 787 323.

Solagum™ L is a carrageenan sold by the company SEPPIC.

Marcol™ 82 is a liquid paraffin sold by the company ESSO.

Lanol™ 84D is dioctyl malate, sold by the company SEPPIC.

Parsol™ MCX is ethylhexyl paramethoxycinnamate sold by the company Givaudan.

Eusolex™ 4360 is 3-benzophenone sold by the company Merck.

Dow Corning™ 245 Fluid is cyclomethicone, sold by the company Dow Corning.

Lipacide™ PVB is a palmitoyl wheat protein hydrolysate sold by the company SEPPIC.

Sepicontrol™ A5 is a mixture of caprylloylglycine, sarcosine and extract of Cinnamon zylanicum, sold by the company SEPPIC, such as those described in international patent application PCT/FR 98/01313 filed on 23 Jun. 1998.

Capigel™ 98 is an acrylic copolymer sold by the company SEPPIC.

Lanol™ 2681 is a coconut caprylate/caprate mixture sold by the company SEPPIC.

The invention claimed is:

1. A self-reversible reverse microlatex composition comprising the following:
   (i) an oil phase;
   (ii) an aqueous phase;
   (iii) at least one water-in-oil (W/O) surfactant;
   (iv) at least one oil-in-water (O/W) surfactant; and
   (v) a branched or a crosslinked polyelectrolyte, wherein, the water-in-oil (W/O) surfactant and the oil-in-water (O/W) surfactant together as a mixture have a total Hydrophile Lipophile Balance (HLB) from about 9.5 to about 10 so to enable formation of a water-in-oil self-reversible reverse microlatex.

2. The composition, according to claim 1, wherein said oil phase is from about 25% to about 50% of the total weight of the composition.

3. The composition, according to claim 2, wherein said oil phase is from about 30% to about 40% of the total weight of the composition.

4. The composition according to claim 1, wherein said polyelectrolyte is from about 15% to about 40% of the total weight of the composition.

5. The composition, according to claim 4, wherein said polyelectrolyte is from about 20% to about 30% of the total weight of the composition.

6. The composition according to claim 1, wherein,
   said polyelectrolyte is at least one homopolymer or copolymer, or a combination thereof,
   said homopolymer is at least one monomer containing a strong acid function, and
   said copolymer is selected from the group consisting of:
   at least one monomer containing a strong acid function copolymerized with at least one monomer containing a weak acid function or with at least one neutral monomer,
   at least one monomer containing a weak acid function copolymerized with at least one neutral monomer, and
   at least one monomer containing a strong acid function copolymerized with a monomer containing at least one weak acid function and with at least one neutral monomer.

7. The composition according to claim 6, wherein said strong acid function is a sulphonic acid or a phosphonic acid.

8. The composition according to claim 7, wherein said strong acid function is partially or totally salified.

9. The composition according to claim 7, wherein said propanesulphonic acid is in the form of a salt selected from the group consisting of an alkali metal salt, an ammonium salt, a monoethanolamine salt, and amino acid salt.

10. The composition according to claim 6, wherein said monomer containing a strong acid function is 2-methyl-2-[(1-oxo-2-propenyl)amino]-1 propanesulphonic acid.

11. The composition according to claim 10, wherein said strong acid function is partially or totally salified.

12. The composition according to claim 6, wherein said monomer containing a weak acid function is a carboxylic acid.

13. The composition according to claim 12, wherein said carboxylic acid of is a weak acid selected from the group consisting of acrylic acid, methacrylic acid, itaconic acid, maleic acid, and 3-methyl-3-[(1-oxo-2-propenyl)amino] butanoic acid.

14. The composition according to claim 13, wherein said acid is partially or totally salified and is selected from the group consisting of alkali metal salt, ammonium salt, monoethanolamine salt, and amino acid salt.

15. The composition according to claim 6, wherein said neutral monomer is selected from the group consisting of: acrylamide, 2-hydroxyethyl acrylate, 2,3-dihydroxypropyl acrylate, 2-hydroxyethyl methacrylate, 2,3-dihydroxypropyl methacrylate, and ethoxylated derivative further comprising a molecular weight comprising of about 400 to about 1,000, of each of the above esters.

16. The composition according to claim 6, wherein said polyelectrolyte is a crosslinked homopolymer which consists of 2methyl-2-[(1-oxo-2-propenyl)amino]-1-propanesulphonic acid.

17. The composition according to claim 16, wherein said propanesulphonic acid is either partially or totally salified in the form of either a sodium salt or an ammonium salt.

18. The composition according to claim 6, wherein said polyelectrolyte is a copolymer of an acrylic acid which consists of either a sodium salt or an ammonium salt that is partially or totally salified and an acrylamide.

19. The composition according to claim 18, wherein said polyelectrolyte consists of said salt and said acrylamide in a molar ratio of from about 10/90 to about 90/10.

20. The composition according to claim 6, wherein said polyelectrolyte is a crosslinked copolymer of 2-methyl-2-[(1-oxo-2-propenyl)amino]-1 -propanesulphonic acid, which is partially or totally salified in one of the forms selected from the group consisting of a sodium salt, an ammonium salt, a monoethanolamine salt, and a lysine salt, and 2-hydroxyethyl acrylate.

21. The composition according to claim 20, wherein said polyelectrolyte consists of said salt and said acrylate in a molar ratio of from about 30/70 to about 90/10.

22. The composition according to claim 21, wherein said polyelectrolyte consists of said salt and said acrylate in a molar ratio of from about 50/50 to about 90/10.

23. The composition according to claim 6, wherein said polyelectrolyte is a crosslinked copolymer of:
(a) a salt of 2-methyl-2-[(1-oxo-2-propenyl)amino]-1-propanesulphonic acid, said salt is selected from the group consisting of a sodium salt, an ammonium salt, a monoethanolamine salt, and a lysine salt, and
(b) acrylic acid, which is either partially or totally salified, in the form of a salt selected from the group consisting of a sodium salt, an ammonium salt, a monoethanolarnine salt and a lysine salt.

24. The composition according to claim 23, wherein said salt from (a) and said acrylic acid in the form of said salt (b) have a molar ratio of from about 30/70 to about 90/10.

25. The composition according to claim 24, wherein said salt from (a) and said acrylic acid from (b) have a molar ratio of from about 30/70 to about 45/55.

26. The composition according to claim 6, wherein said polyelectrolyte is a crosslinked copolymer of a sodium salt or an ammonium salt of 2-methyl-2-[(1-oxo-2-propenyl) amino]-1-propanesulphonic acid and an acrylamide.

27. The composition according to claim 26, wherein said polyelectrolyte consists of said salt and said acrylamide in a molar ratio of from about 50/50 to about 30/70.

28. The composition according to claim 6, wherein said polyelectrolyte is a crosslinked copolymer of:
(a) salt of 2-methyl-2-[(1-oxo-2-propenyl)amino]-1-propanesulphonic acid, said salt is selected from the group consisting of a sodium salt, an ammonium salt, a monoethanolamine salt, and a lysine salt,
(b) an acrylic acid, which is partially or totally salified, in the form of a salt selected from the group consisting of an ammonium salt, a monoethanolamine salt, and a lysine salt, and
one of (c) an acrylamide and (d) a 2-hydroxyethyl acrylate.

29. The composition according to claim 28, wherein said crosslinked copolymer consists of (a)/(b)+(c) or (a)/(b)+(d) molar proportions from between about 10/90 to about 90/10 and (b)/(c) or (b)/(d) molar proportions from between about 10/90 to about 90/10.

30. The composition according to claim 6, wherein said polyelectrolyte is comprised of a crosslinked copolymer and/or alternatively branched with a diethylenic or polyethylenic compound in a molar proportion, expressed relative to the monomers used, from about 0.005% to about 1%.

31. The composition according to claim 6, wherein said polyelectrolyte is comprised of a crosslinked copolymer and/or alternatively branched with a diethylenic or polyethylenic compound in a molar proportion, expressed relative to the monomers used, from about 0.01% to about 0.5%.

32. The composition according to claim 31, wherein said polyelectrolyte is comprised of a crosslinked copolymer and/or alternatively branched with a diethylenic or polyethylenic compound in a molar proportion, expressed relative to the monomers used, from about 0.1% to about 0.25%.

33. The composition according to claim 6, said crosslinking agent and/or the branching agent further consists of a diallyloxy acetic acid or a salt thereof or a mixture thereof of the composition.

34. The composition according to claim 33, wherein said diallyloxy acetic acid or a salt or a mixture thereof is selected from the group consisting of: sodium diallyloxyacetate, ethylene glycol dimethacrylate, ethylene glycol diacrylate, diallylurea, trimethylolpropane triacrylate, methylenebis(acrylamide), triallylamine and diallyl tartramide.

35. The composition according to claim 1, wherein said composition may be employed in the cosmetic, dermopharmaceutical, and/or pharmaceutical industries.

36. The composition according to claim 1, said composition may be employed as a thickener and/or emulsifier in preparations for industries selected from the group consisting of the textile industry, the paper industry, and the paint manufacturing industry, or as a thickener for printing pastes based on pigments or dyes.

* * * * *